US012766039B2

(12) United States Patent
Stephany et al.

(10) Patent No.: US 12,766,039 B2
(45) Date of Patent: Oct. 20, 2026

(54) ARTICLE OF PERSONAL PROTECTIVE EQUIPMENT, SYSTEM, COMPUTING DEVICE, AND COMPUTER-IMPLEMENTED METHOD

(71) Applicant: 3M INNOVATIVE PROPERTIES COMPANY, St. Paul, MN (US)

(72) Inventors: Gary R. Stephany, Stillwater, MN (US); Michael G. Wurm, Waukesha, WI (US); Eric J. Larson, Bayport, MN (US); Shane A. Hainey, Cottage Grove, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 108 days.

(21) Appl. No.: 18/852,068

(22) PCT Filed: Mar. 20, 2023

(86) PCT No.: PCT/IB2023/052723
§ 371 (c)(1),
(2) Date: Sep. 27, 2024

(87) PCT Pub. No.: WO2023/187549
PCT Pub. Date: Oct. 5, 2023

(65) Prior Publication Data
US 2025/0205088 A1 Jun. 26, 2025

Related U.S. Application Data

(60) Provisional application No. 63/362,339, filed on Apr. 1, 2022.

(51) Int. Cl.
*A61F 11/14* (2006.01)
*H04R 3/00* (2006.01)

(52) U.S. Cl.
CPC ............ *A61F 11/145* (2022.01); *H04R 3/005* (2013.01); *H04R 2410/05* (2013.01)

(58) Field of Classification Search
CPC .... A61F 11/145; H04R 3/005; H04R 2410/05
See application file for complete search history.

(56) References Cited

U.S. PATENT DOCUMENTS 9,247,204 B1 1/2016 Yin et al.
11,010,126 B1 * 5/2021 Song .................... H04R 29/001
(Continued)

OTHER PUBLICATIONS

International Search report for PCT International Application No. PCT/IB2023/052723, mailed on Aug. 14, 2023, 3 pages.

*Primary Examiner* — Paul W Huber
(74) *Attorney, Agent, or Firm* — Katherine M. Scholz

(57) ABSTRACT

An article of a personal protective equipment includes at least one microphone, a memory, and a processor communicably coupled to each of the at least one microphone and the memory. The at least one microphone is configured to generate one or more audio streams. The memory is configured to store a threshold score. The processor is configured to: receive the one or more audio streams; determine a score for the one or more audio streams based on one or more evaluation parameters; compare the score with the threshold score stored in the memory; and mute the at least one microphone when the score of the one or more audio streams crosses the threshold score.

7 Claims, 11 Drawing Sheets

(56) References Cited

U.S. PATENT DOCUMENTS

| | | | | |
|---|---|---|---|---|
| 11,568,643 | B2 * | 1/2023 | Powderly | G02B 27/0172 |
| 11,778,364 | B2 * | 10/2023 | Bonanno | A63F 13/24<br>381/311 |
| 12,175,960 | B2 * | 12/2024 | Copt | A61F 11/14 |
| 12,354,587 | B2 * | 7/2025 | Morton | H04R 1/1083 |
| 2013/0051590 | A1 | 2/2013 | Slater | |
| 2018/0047414 | A1 | 2/2018 | Kasilya et al. | |
| 2019/0278556 | A1 | 9/2019 | Usher et al. | |

* cited by examiner

ARTICLE OF PERSONAL PROTECTIVE EQUIPMENT, SYSTEM, COMPUTING DEVICE, AND COMPUTER-IMPLEMENTED METHOD

CROSS-REFERENCE TO RELATED APPLICATIONS

This Application is a national stage filing under 35 U.S.C. § 371 of PCT/IB2023/0527223, filed 20 Mar. 2023, which claims the benefit of Provisional U.S. Patent Application No. 63/362,339, filed 1 Apr. 2022, the entire disclosure of each of which is incorporated herein by reference.

TECHNICAL FIELD

The present disclosure relates to an article of personal protective equipment (PPE), a communication system, a computing device for controlling a plurality of articles of PPE, and a computer-implemented method for controlling the plurality of articles of PPE.

BACKGROUND

An article of personal protective equipment (PPE) may be used by personnel (e.g., emergency responders) working in a high-noise environment to prevent high noises from entering ears of the personnel. However, the high noises may reach the ears of the personnel in case of an improper fit of the article of PPE. In some cases, the article of PPE may also include a communication device to communicate audio streams with other personnel in the high-noise environment. However, the high noises may also leak into the audio streams due to the improper fit.

SUMMARY

According to a first aspect, the present disclosure provides an article of personal protective equipment (PPE). The article of PPE includes at least one microphone configured to generate one or more audio streams. The article of PPE further includes a memory configured to store a threshold score. The article of PPE further includes a processor communicably coupled to each of the at least one microphone and the memory. The processor is configured to receive the one or more audio streams. The processor is further configured to determine a score for the one or more audio streams based on one or more evaluation parameters. The processor is further configured to compare the score with the threshold score stored in the memory. The processor is further configured to mute the at least one microphone when the score of the one or more audio streams crosses the threshold score.

According to a second aspect, the present disclosure provides a communication system. The communication system includes a plurality of articles of PPE. Each of the plurality of articles of PPE includes at least one microphone configured to generate one or more audio streams. Each of the plurality of articles of PPE further includes a transceiver configured to transmit the one or more audio streams. The communication system further includes a memory configured to store at least one threshold score. The communication system further includes a hub communicably coupled to each of the memory and the transceiver of each of the plurality of articles of PPE. For each article of PPE from the plurality of articles of PPE, the hub is configured to: receive the one or more audio streams; determine a score for the one or more audio streams based on one or more evaluation parameters; compare the score with the at least one threshold score stored in the memory; generate a mute signal when the score of the one or more audio streams crosses the at least one threshold score; and transmit the mute signal to the transceiver of the corresponding article of PPE for which the score crosses the at least one threshold score. Each article of PPE from the plurality of articles of PPE is configured to mute the corresponding at least one microphone upon receiving the mute signal from the hub.

According to a third aspect, the present disclosure provides a computing device for controlling a plurality of articles of PPE. The computing device includes a memory configured to store at least one threshold score. The computing device further includes a processor communicably coupled to the memory. The processor is configured to receive a plurality of audio streams transmitted from the plurality of articles of PPE. Each of the plurality of audio streams is transmitted by a corresponding article of PPE from the plurality of articles of PPE. The processor is further configured to determine a plurality of scores based on one or more evaluation parameters. The plurality of scores corresponds to the plurality of audio streams. The processor is further configured to compare the plurality of scores with at least one threshold score stored in the memory. The processor is further configured to generate a mute signal when at least one score from the plurality of scores corresponding to at least one audio stream from the plurality of audio streams crosses the at least one threshold score. The processor is further configured to transmit the mute signal to the at least one article of PPE transmitting the at least one audio stream. The at least one article of PPE is configured to mute at least one microphone upon receiving the mute signal.

According to a fourth aspect, the present disclosure provides a computer-implemented method for controlling a plurality of articles of PPE. The computer-implemented method includes receiving a plurality of audio streams transmitted from the plurality of articles of PPE, each of the plurality of audio streams being transmitted by a corresponding article of PPE from the plurality of articles of PPE. The computer-implemented method further includes determining a plurality of scores based on one or more evaluation parameters. The plurality of scores corresponds to the plurality of audio streams. The computer-implemented method further includes comparing the plurality of scores with at least one threshold score. The computer-implemented method further includes generating a mute signal when at least one score from the plurality of scores corresponding to at least one audio stream from the plurality of audio streams crosses the at least one threshold score. The computer-implemented method further includes transmitting the mute signal to the at least one article of PPE transmitting the at least one audio stream.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

Exemplary embodiments disclosed herein may be more completely understood in consideration of the following detailed description in connection with the following figures. The figures are not necessarily drawn to scale. Like numerals used in the figures refer to like components. When referring to the elements collectively or to a non-specific one or more of the elements, the small letter designation may be eliminated. However, it will be understood that the use of a number to refer to a component in a given figure is not intended to limit the component in another figure labeled with the same number.

DETAILED DESCRIPTION

Figure 1:
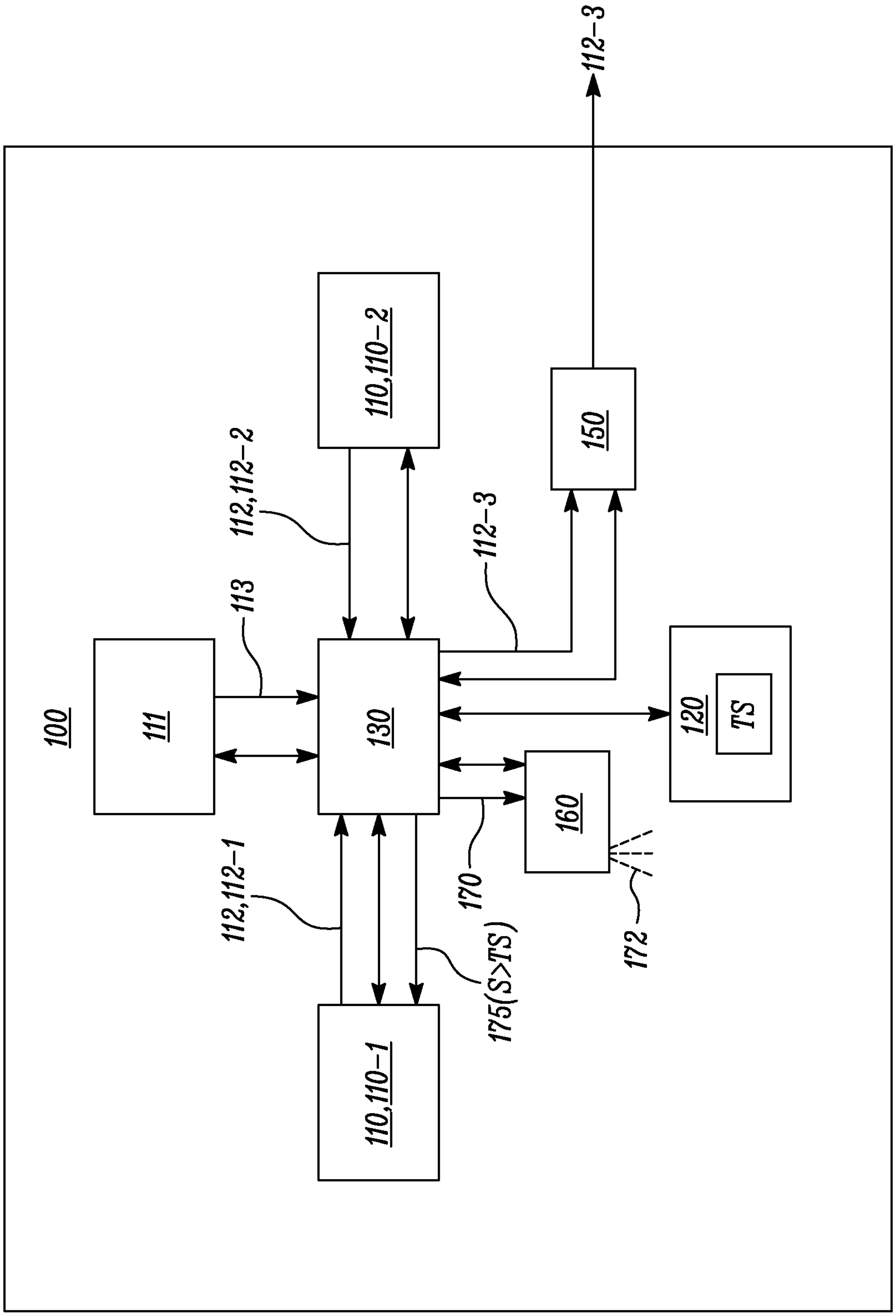
FIG. 1 illustrates a schematic block diagram of an article of PPE, in accordance with an embodiment of the present disclosure.

In the following description, reference is made to the accompanying figures that form a part thereof and in which various embodiments are shown by way of illustration. It is to be understood that other embodiments are contemplated and may be made without departing from the scope or spirit of the present disclosure. The following detailed description, therefore, is not to be taken in a limiting sense.

In the following disclosure, the following definitions are adopted.

As used herein, all numbers should be considered modified by the term "about". As used herein, "a," "an," "the," "at least one," and "one or more" are used interchangeably.

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties).

As used herein, the terms "first" and "second" are used as identifiers. Therefore, such terms should not be construed as limiting of this disclosure. The terms "first" and "second" when used in conjunction with a feature or an element can be interchanged throughout the embodiments of this disclosure.

As used herein, "at least one of A and B" should be understood to mean "only A, only B, or both A and B".

As used herein, the term "configured to" and like is at least as restrictive as the term "adapted to" and requires actual design intention to perform the specified function rather than mere physical capability of performing such a function.

As used herein, the term "communicably coupled to" refers to direct coupling between components and/or indirect coupling between components via one or more intervening components. Such components and intervening components may comprise, but are not limited to, junctions, communication paths, components, circuit elements, circuits, functional blocks, and/or devices. As an example of indirect coupling, a signal conveyed from a first component to a second component may be modified by one or more intervening components by modifying the form, nature, or format of information in a signal, while one or more elements of the information in the signal are nevertheless conveyed in a manner than can be recognized by the second component As used herein, the term "signal," includes, but is not limited to, one or more electrical signals, optical signals, electromagnetic signals, analog and/or digital signals, one or more computer instructions, a bit and/or bit stream, or the like.

As used herein, the term "communication device" generally includes a transceiver, and/or other devices for communicating with other devices directly or via a network, and/or a user interface for communicating with one or more users.

As used herein, the term "duplex" may refer to a point-to-point communication system composed of two or more connected parties or devices that can communicate with one another in both directions.

As used herein, the term "remote server" refers to a computer that is outside a given geographical location and provides resources, data, services, or programs to other computers, known as clients, over a network.

As used herein, the term "fit" is indicative of a position of an article of PPE on a wearer.

As used herein, the term "fit quality" indicates if the article of PPE provides a proper/good fit or an improper/poor fit. The good fit quality indicates the article of PPE provides a protection expected from the article of PPE, as indicated by its manufacturer. On the other hand, the poor fit quality indicates the article of PPE may not provide the protection expected from the article of PPE, as indicated by its manufacturer.

As used herein, "proper/good fit" indicates that the article of PPE is positioned correctly. For example, for earplugs, the proper fit indicates that the earplug is placed inside the ear canal, expanding to the walls of the ear canal. Further, for earmuffs, the proper fit indicates that the earmuff covers the ears of wearer completely without any gaps between cushions of the earmuff and the wearer's skin.

As used herein, the term "hazardous or potentially hazardous environmental conditions" may refer to environmental conditions that may be harmful to a human being, such as high noise levels, high ambient temperatures, lack of oxygen, presence of explosives, exposure to radioactive or biologically harmful materials, and exposure to other hazardous substances. Depending upon the type of safety equipment, environmental conditions and physiological conditions, corresponding thresholds or levels may be established to help define hazardous and potentially hazardous environmental conditions.

As used herein, the term "hazardous or potentially hazardous environments" may refer to environments that include hazardous or potentially hazardous environmental conditions. The hazardous or potentially hazardous environments may include, for example, chemical environments, biological environments, nuclear environments, fires, industrial sites, construction sites, agricultural sites, mining sites, or manufacturing sites.

As used herein, "an article of personal protective equipment (PPE)" may include any type of equipment or clothing that may be used to protect a user from hazardous or potentially hazardous environmental conditions. In some examples, one or more individuals, such as the users, may utilize the article of PPE while engaging in tasks or activities within the hazardous or potentially hazardous environment. Examples of the articles of PPE may include, but are not limited to, hearing protection (including ear plugs and ear muffs), respiratory protection equipment (including disposable respirators, reusable respirators, powered air purifying respirators, self-contained breathing apparatus and supplied air respirators), facemasks, oxygen tanks, air bottles, protective eyewear, such as visors, goggles, filters or shields (any of which may include augmented reality functionality), protective headwear, such as hard hats, hoods or helmets, protective shoes, protective gloves, other protective clothing, such as coveralls, aprons, coat, vest, suits, boots and/or gloves, protective articles, such as sensors, safety tools, detectors, global positioning devices, mining cap lamps, fall protection harnesses, exoskeletons, self-retracting lifelines, heating and cooling systems, gas detectors, and any other suitable gear configured to protect the users from injury. The articles of PPE may also include any other type of clothing or device/equipment that may be worn or used by the users to protect against extreme noise levels, extreme temperatures, fire, reduced oxygen levels, explosions, reduced atmospheric pressure, radioactive, and/or biologically harmful materials.

As used herein, the terms "responder" or "emergency responder" refer to any person or persons responsible for addressing an emergency situation, such as firefighters, first responders, healthcare professionals, paramedics, HAZMAT workers, security personnel, law enforcement personnel, or any other personnel working in the hazardous environment.

An article of personal protective equipment (PPE) may be used by a user (e.g., an emergency responder) working in a hazardous environment. In some cases, the hazardous environment may expose the user to harmful noises and therefore is a noisy environment. The article of PPE may protect the user from such harmful noises in the noisy environment. However, in order to protect the user from harmful noises, a fit of the article of PPE should be a proper or a good fit. The proper fit provides an expected Noise Reduction Rating (NRR) as indicated by a manufacturer. Sometimes, the user may not position the article of PPE as intended and therefore, the fit of the article of PPE may be an improper or a poor fit. The article of PPE which have the improper fit may not provide the expected NRR, as required in the noisy environment. Specifically, the harmful noises may leak into ears of the user.

Further, in some cases, the article of PPE may also allow the user to communicate with other users in the noisy environment or communicate with a central base station. In other words, the article of PPE may also be a communication device. In such cases, the harmful noises leaking into the ears of the user due to the poor fit may also leak into microphone(s) of the article of PPE. This may lead to the harmful noises leaking into audio streams generated by the microphone(s) of the article of PPE which are subsequently transmitted to the other users. This may be detrimental for an effective communication between the user and the other users, as well as ears of the other users. Therefore, it may be crucial to prevent such harmful noises to enter into the ears of the user, as well as in the audio streams to be transmitted to the other users.

The present disclosure relates to an article of personal protective equipment (PPE), a communication system, a computing device for controlling a plurality of articles of PPE, and a computer-implemented method for controlling the plurality of articles of PPE.

In an embodiment, the article of PPE includes at least one microphone configured to generate one or more audio streams. The article of PPE further includes a memory configured to store a threshold score. The article of PPE further includes a processor communicably coupled to each of the at least one microphone and the memory. The processor is configured to receive the one or more audio streams. The processor is further configured to determine a score for the one or more audio streams based on one or more evaluation parameters. The processor is further configured to compare the score with the threshold score stored in the memory. The processor is further configured to mute the at least one microphone when the score of the one or more audio streams crosses the threshold score.

Therefore, the article of PPE of the present disclosure may determine the fit of the article of PPE by detecting the harmful noises based on the score of the one or more audio streams. Further, the processor of the article of PPE may mute the at least one microphone when the score of the one or more audio streams crosses the threshold score, such that the one or more audio streams are not generated by the at least one microphone and therefore not transmitted to the other users. This may prevent the harmful noises from being transmitted to the other users and therefore protect the ears of the other users and/or enhance the communication between the other users.

Further, in some cases, the processor may also generate an alert for the user of the article of PPE to notify them that they need to improve the fit of the article of PPE. The user may then improve the fit of the article of PPE to prevent the harmful noises from entering the ears.

The communication system of the present disclosure includes a plurality of articles of PPE. Each of the plurality of articles of PPE includes at least one microphone configured to generate one or more audio streams. Each of the plurality of articles of PPE further includes a transceiver configured to transmit the one or more audio streams. The communication system further includes a memory configured to store at least one threshold score. The communication system further includes a hub communicably coupled to each of the memory and the transceiver of each of the plurality of articles of PPE. For each article of PPE from the plurality of articles of PPE, the hub is configured to: receive the one or more audio streams; determine a score for the one or more audio streams based on one or more evaluation parameters; compare the score with the at least one threshold score stored in the memory; generate a mute signal when the score of the one or more audio streams crosses the at least one threshold score; and transmit the mute signal to the transceiver of the corresponding article of PPE for which the score crosses the at least one threshold score. Each article of PPE from the plurality of articles of PPE is configured to mute the corresponding at least one microphone upon receiving the mute signal from the hub.

Further, the computing device for controlling the plurality of articles of PPE may be substantially similar to the hub of the communication system. However, the computing device further includes the memory of the communication system.

In some cases, the plurality of articles of PPE may be in a duplex communication with each other. The audio streams from each article of PPE may be transmitted to the hub in addition to being transmitted to the other articles of PPE from the plurality of articles of PPE. Further, the hub of the present disclosure may determine the fit of the article of PPE by detecting the harmful noises based on the score of the one or more audio streams received from each article of PPE. Further, the hub may generate the mute signal to mute the at least one microphone when the score of the one or more audio streams crosses the threshold score, such that the one or more audio streams are not generated by the at least one microphone and therefore are not transmitted to the other articles of PPE. This may prevent the harmful noises from being transmitted to the other articles of PPE and protect the ears of the other users of the other articles of PPE, while also enhancing the communication between the users of the plurality of articles of PPE.

Further, in some cases, the hub may also generate an alert signal for the user of the article of PPE corresponding to the at least one microphone. The user of the article of PPE corresponding to the at least one microphone may then improve the fit of the article of PPE and thereby prevent the harmful noises from entering the ears.

In some cases, the hub and/or the computing device of the present disclosure may also mix all the received audio streams and transmit the mixed audio stream to the plurality of articles of PPE. Therefore, an audio stream including the harmful noises due to the improper fit may also corrupt the mixed audio stream. The communication system including the hub and/or the computing device may therefore prevent the audio stream including the harmful noises from being generated and corrupting the mixed audio stream. Thus, the users of the other articles of PPE may communicate effectively with each other.

Referring now to the figures, FIG. 1 is a schematic block diagram of an article of personal protective equipment (PPE) 100, according to an embodiment of the present disclosure. The article of PPE 100 may interchangeably be referred to as "the article 100". In some embodiments, the article 100 is a hearing protection device (HPD). In some embodiments, the HPD includes an in-ear HPD, an over-ear HPD, or an on-ear HPD. Examples of the HPD include, but are not limited to, ear plugs and earmuffs. The HPDs may be used by a user to reduce exposure to harmful noises in an environment, such as a noisy environment. Further, the article 100 may only be effective if it is properly worn by the user in order to provide a proper fit quality, i.e., a fit of the article 100 is a proper/good fit. The proper fit quality indicates the article 100 provides an expected Noise Reduction Rating (NRR) as indicated by a manufacturer. The NRR may be defined as a unit of measurement used to determine an effectiveness of the HPD to decrease sound exposure within a given working environment. Sometimes, the user may not position the article 100 as intended and therefore, the fit of the article 100 may be an improper or a poor fit.

In some embodiments, the article 100 may allow communication with other users in the environment or a remote server. In other words, the article 100 may also be a communication device.

The article 100 includes at least one microphone 110. In some embodiments, the at least one microphone 110 is configured to be placed proximal to or inside ears of the user. The at least one microphone 110 is configured to generate one or more audio streams 112. In some embodiments, the one or more audio streams 112 include a speech component of a speech of the user of the article 100. In some cases, due to the improper fit of the article 100, the one or more audio streams 112 may also include a noise component of an ambient noise in the environment. In some cases, the ambient noise maybe harmful noises that may harm the user.

The article 100 further includes a memory 120 configured to store a threshold score TS. The threshold score TS may be a predetermined score above or below which the one or more audio streams 122 may be detrimental to the ears of the user and/or an effective communication with the other users in the environment.

The article 100 further includes a processor 130 communicably coupled to each of the at least one microphone 110 and the memory 120. In some embodiments, the processor 130 may include any suitable data processor for processing data. For example, the processor 130 may include a microprocessor, a microcontroller, a computer, or other suitable devices that control operation of devices and execute programs. Various other examples of the processor 130 include central processing units ("CPUs"), microcontrollers, programmable logic devices, field programmable gate arrays, digital signal processing ("DSP") devices, and the like. The processor 130 may include any general variety device such as a reduced instruction set computing ("RISC") device, a complex instruction set computing ("CISC") device, or a specially designed processing device, such as an application-specific integrated circuit ("ASIC") device.

In some embodiments, the memory 120 may include a hard disk that magnetically or electronically stores instructions and electrically loads various programs related to a process from the hard disk when the processor 130 executes the instructions. The memory 120 may include an auxiliary storage device that can read information stored in a storage medium, such as a CD-ROM, a DVD-ROM, or the like.

In some embodiments, the article 100 further includes an external microphone 111 communicably coupled to the processor 130. The external microphone 111 may be positioned anywhere distal to and/or outside the ears of the user. The external microphone 111 is configured to generate one or more ambient audio streams 113. The one or more ambient audio streams 113 may include the ambient noise and/or the harmful noise in the environment. Therefore, the one or more ambient audio streams 113 may be used to determine ambient noise levels. In some embodiments, the processor 130 is configured to adjust the threshold score TS at least based on the one or more ambient audio streams 113. For example, the processor 130 may increase or decrease the threshold score TS at least based on the ambient noise levels.

The processor 130 is configured to receive the one or more audio streams 112. The processor 130 is further configured to determine a score S for the one or more audio streams 112 based on one or more evaluation parameters 140 (shown in FIGS. 2A-2C). The score S may be indicative of the fit of the article 100. Further, the score S may further be used to determine if the one or more audio streams 112 are detrimental to the ears of the user and/or the effective communication.

The processor 130 is further configured to compare the score S with the threshold score TS stored in the memory 120. The processor 130 is further configured to mute the at least one microphone 110 when the score S of the one or more audio streams 112 crosses the threshold score TS. It should be noted that the phrase "the score S crosses the threshold score TS" may refer to the score S being greater than the threshold score TS or being less than the threshold score TS, as per desired application attributes. In some embodiments, the processor 130 is further configured to mute the at least one microphone 110 when the score S of the one or more audio streams 112 is greater than or equal to the threshold score TS or less than or equal to the threshold score TS. Therefore, the one or more audio streams 112 are not generated by the at least one microphone 110 and thereby not transmitted to the other users. This may prevent the harmful noises from being transmitted to the other users and therefore protect the ears of the other users and/or enhance the communication between the other users.

In some embodiments, the at least one microphone 110 includes a plurality of microphones spaced apart from each other. In some examples, the plurality of microphones may be left and right microphones of the article 100 configured to be inserted in left and right ears of the user, respectively. However, the at least one microphones may include any number of microphones as per desired application attributes.

The processor 130 is communicably coupled to each of the plurality of microphones. In some embodiments, the one or more audio streams 112 includes a plurality of audio streams. In some embodiments, each of the plurality of microphones is configured to generate a corresponding audio stream from the plurality of audio streams. For example, in the illustrated embodiment of FIG. 1, the at least one microphone 110 includes two microphones 110-1, 110-2 spaced apart from each other. Further, the one or more audio streams 112 includes two audio streams 112-1, 112-2. Each of the two microphones 110-1, 110-2 is configured to generate a corresponding audio stream from the two audio streams 112-1, 112-2. Specifically, the microphone 110-1 is configured to generate the audio stream 112-1 and the microphone 110-2 is configured to generate the audio stream 112-2.

In some embodiments, the processor 130 is further configured to receive the plurality of audio streams generated by the plurality of microphones. In some embodiments, the processor 130 is further configured to determine the score S for each of the plurality of audio streams based on the one or more evaluation parameters 140 (shown in FIGS. 2A-2C). In some embodiments, the processor 130 is further configured to compare the score S for each of the plurality of audio streams with the threshold score TS stored in the memory 120. In some embodiments, the processor 130 is further configured to mute one or more microphones from the plurality of microphones corresponding to the one or more audio streams for which the score S crosses the threshold score TS.

For example, in the illustrated embodiment of FIG. 1, the processor 130 receives the audio streams 112-1, 112-2 generated by the microphones 110-1, 110-2, respectively. Further, the processor 130 determines the score S for each of the audio streams 112-1, 112-2 based on the one or more evaluation parameters 140 (shown and described with respect to FIGS. 2A-2C). The processor 130 further compares the score S for each of the audio streams 112-1, 112-2 with the threshold score TS stored in the memory 120.

In the illustrated embodiment of FIG. 1, the score S of the audio stream 112-1 crosses the threshold score TS and the score S of the audio stream 112-2 does not cross the threshold score TS. Therefore, the processor 130 mutes the microphone 110-1 from the microphones 110-1, 110-2 corresponding to the audio stream 112-1 for which the score S crosses the threshold score TS.

In some embodiments, the processor 130 is configured to generate a mute signal 175 when the score S of the one or more audio streams 112 crosses the at least one threshold score TS. Further, the processor 130 is configured to transmit the mute signal 175 to the one or more microphones from the plurality of microphones corresponding to the one or more audio streams for which the score S crosses the threshold score TS. The mute signal 175 may cause a muting circuit (not shown) to perform mute processing to stop an input of an audio stream into the microphone 110, for example, by zeroing a signal or by omitting the signal from a mixer. In some embodiments, the mute signal 175 may cause a switch or a gate to open a connection between an element and a receiver of the microphone 110. In some embodiments, the mute signal 175 may cause any audio stream generated by the microphone 110 to not be played (muted) locally, or if the audio stream is transmitted to the one or more external devices, causing the audio stream generated by the microphone 110 to not be played (muted) or discarded by the one or more external devices.

In the illustrated example of FIG. 1, the phrase "the score S crosses the threshold score TS" refer to the score S being greater than the threshold score TS. Therefore, in the illustrated embodiment of FIG. 1, the processor 130 transmits the mute signal 175 to the microphone 110-1 from the microphones 110-1, 110-2 corresponding to the audio stream 112-1 for which the score S crosses the threshold score TS. This may prevent the harmful noises from being transmitted to the other users and therefore prevent the ears of the other users and/or enhance the communication between the other users.

In some embodiments, the article 100 further includes an output device 160 communicably coupled to the processor 130. The processor 130 is further configured to generate an alert signal 170 when the score S crosses the threshold score TS. The output device 160 is configured to generate an alert 172 upon receiving the alert signal 170 from the processor 130. In some embodiments, the output device 160 is at least one of a speaker, a light emitting diode (LED), and a motor. In some embodiments, the alert 172 is at least one of an audio alert, a visual alert, and a haptic alert. Thus, the alert 172 may notify the user of the improper fit of the article 100 and thereby the user may improve the fit of the article 100 to prevent the harmful noises from entering the ears.

In some embodiments, the article 100 further includes a transceiver 150. In some embodiments, the transceiver 150 is communicably coupled to the processor 130. The transceiver 150 is configured to transmit the one or more audio streams 112 (for example, the audio streams 112-1, 112-2). In some embodiments, the transceiver 150 is configured to transmit the one or more audio streams 112 to one or more external devices (not shown). In some embodiments, the one or more external devices may include the other articles of PPE in the environment. In some other embodiments, the one or more external devices may include the remote server and/or a hub.

In some embodiments, the processor 130 is further configured to combine the plurality of audio streams prior to transmitting the plurality of audio streams. For example, the processor 130 may be configured to combine the audio streams 112-1, 112-2 to generate an audio stream 112-3. In the illustrated embodiment of FIG. 1, the transceiver 150 is configured to transmit the audio stream 112-3.

Figure 2A:
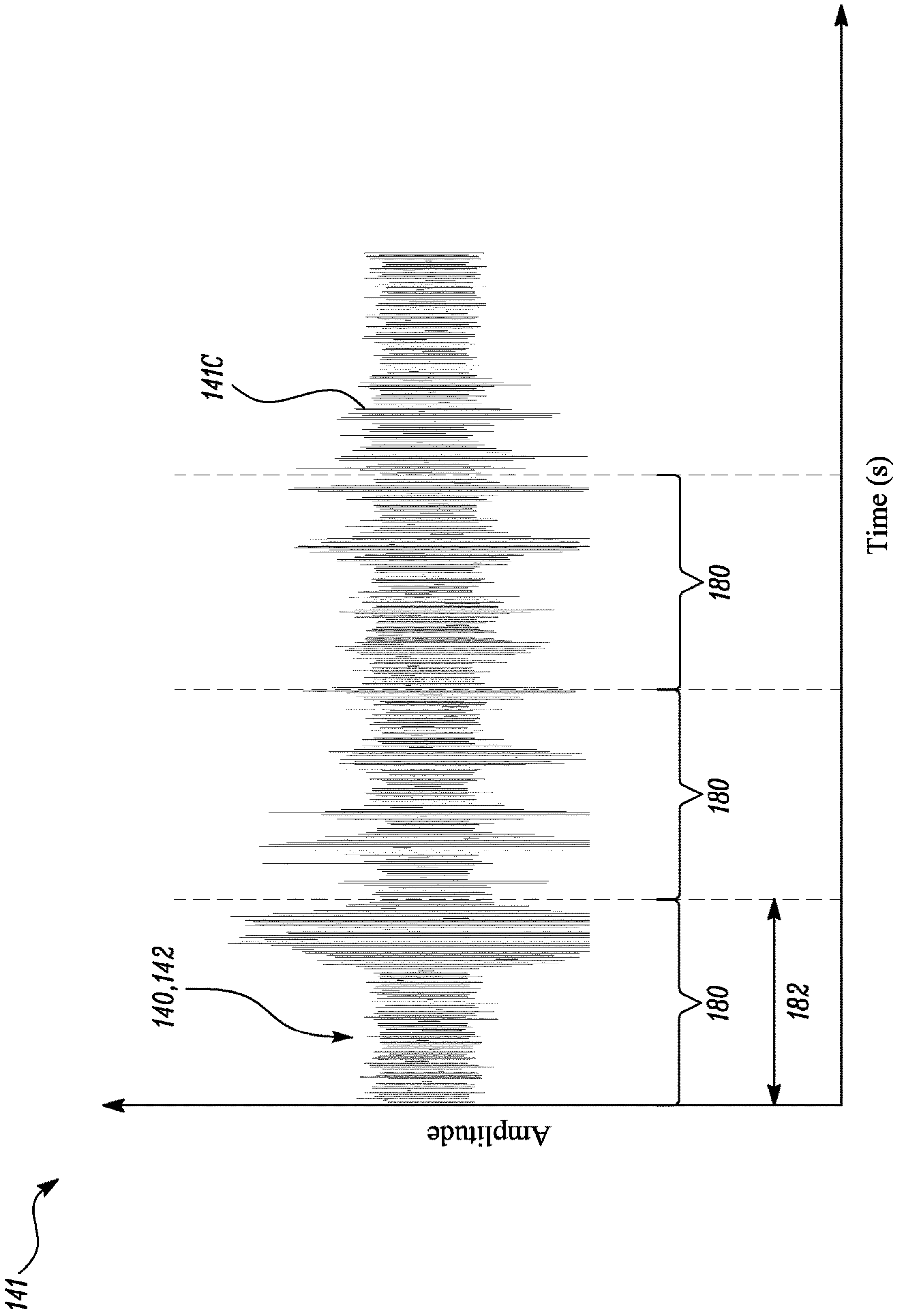
FIG. 2A illustrates a plot depicting amplitude versus time of an audio stream, in accordance with an embodiment of the of the present disclosure.

FIG. 2A illustrates an exemplary plot 141 depicting amplitude versus time of an audio stream from the one or more audio streams 112 (shown in FIG. 1). Time is expressed in seconds(s) in the abscissa. Amplitude is shown in the ordinate in arbitrary units. The plot 141 includes a curve 141C representative of the audio stream with respect to time.

Referring now to FIGS. 1 and 2A, in some examples, the audio stream may be the audio stream 112-1 or the audio stream 112-2. In some embodiments, the processor 130 is further configured to segment the one or more audio streams 112 into one or more segments 180 of a predetermined interval 182. In some embodiments, the predetermined interval 182 is from about 1 millisecond (ms) to about 30 seconds(s). In some embodiments, the predetermined interval 182 is about 16 ms. In some embodiments, the predetermined interval 182 is about 1 s, about 10 s, about 15 s, about 20 s, about 25 s, or about 30 s. However, in some other embodiments, the predetermined interval 182 may be of any time duration as per desired application attributes.

In some embodiments, the processor 130 is further configured to determine the score S for the one or more segments 180 of the one or more audio streams 112. In some embodiments, the processor 130 is further configured to determine the score S for each of the one or more segments 180 of the one or more audio streams 112.

In some embodiments, the one or more evaluation parameters 140 include a corresponding baseline noise level 142 of each of the one or more audio streams 112. In some embodiments, the processor 130 is configured to determine the score S for the one or more audio streams 112 based on the corresponding baseline noise level 142 of each of the one or more audio streams 112.

For example, in the illustrated embodiment of FIG. 2A, the processor 130 is configured to determine the score S for the audio stream based on the baseline noise level 142 of the audio stream. In some embodiments, the processor 130 is configured to determine the score S for each of the segments 180 of the audio stream based on the corresponding baseline noise level 142 of each of the segments 180 of the audio stream.

The baseline noise level 142 is typically an estimate of an average noise of the noise component that may be present in the one or more audio streams 112, without the speech component of the user. The baseline noise level 142 may be a function of the fit of the article 100. Further, the baseline noise level 142 may be a function of the ambient noise levels. Therefore, in order to determine the baseline noise levels 142, the processor 130 may determine and/or obtain the ambient noise levels. In some embodiments, the processor 130 may determine the ambient noise levels using the one or more ambient audio streams 113 generated by the external microphone 111. In some other embodiments, the processor 130 may receive the ambient noise levels from one or more external devices (not shown), such as a hub, a remote server, other articles of PPE in the environment, and so forth. In some cases, the threshold score TS may be adjusted based on the ambient noise levels.

In some examples, the baseline noise level 142 may be determined using a non-linear filter with independent rise and fall time constants. The rise and fall time constants may be used to reduce sensitivity to transient noise and focus on long-term baseline noise.

In one example, the non-linear filter is according to the equation provided below:

$$y[n] = \begin{cases} \text{if RMS value} > y[n-1], & c_{rise}y[n-1] + (1-c_{rise})x[n] \\ \text{else} & c_{fall}y[n-1] + (1-c_{fall})x[n] \end{cases} \quad (1)$$

where, $y[n]$ is RMS value of the baseline noise of current segment;

$y[n-1]$ is RMS value of the baseline noise of previous segment;

$x[n]$ is RMS value of the audio stream;

$c_{rise}$ is rise time constant; and $c_{fall}$ is fall time constant.

Figure 2B:
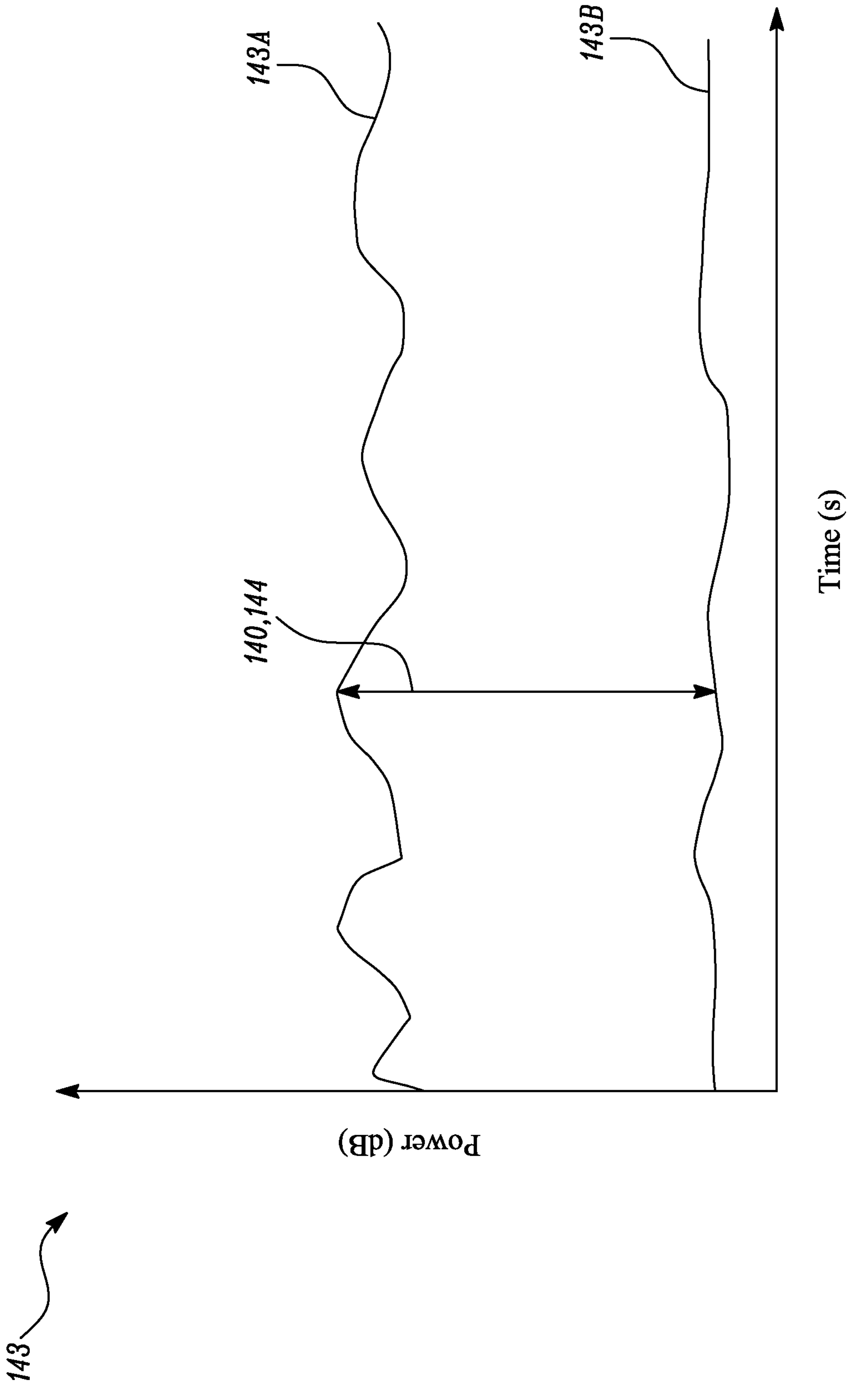
FIG. 2B illustrates a plot depicting estimated speech power versus time of an audio stream and estimated noise power versus time of the audio stream, in accordance with an embodiment of the present disclosure.

FIG. 2B illustrates an exemplary plot 143 depicting estimated signal power versus time of the speech component of an audio stream from the one or more audio streams 112 (shown in FIG. 1) and estimated signal power versus time of the noise component of the same audio stream. Time is expressed in seconds(s) in the abscissa. Power is expressed in decibels (dB) in the ordinate.

The plot 143 includes a curve 143A representative of the estimated signal power of the speech component of the audio stream with respect to time. The plot 143 further includes a curve 143B representative of the estimated signal power of the noise component of the audio stream with respect to time.

Referring now to FIGS. 1 and 2B, in some examples, the audio stream may be the audio stream 112-1 or the audio stream 112-2. In some embodiments, the one or more evaluation parameters 140 include a corresponding signal-to-noise ratio (SNR) 144 for each of the one or more audio streams 112. In some embodiments, the processor 130 is configured to determine the score S for the one or more audio streams 112 based on the corresponding SNR 144 for each of the one or more audio streams 112.

For example, in the illustrated embodiment of FIG. 2B, the processor 130 is configured to determine the score S for the audio stream based on the SNR 144 of the audio stream. In some embodiments, the processor 130 is configured to determine the score S for each of the segments 180 (shown in FIG. 2A) of the audio stream based on the corresponding SNR 144 of each of the segments 180 of the audio stream.

The SNR 144 is a ratio of the estimated signal power of the speech component of the audio stream to the estimated signal power of the noise component of the audio stream. Typically, the SNR 144 is measured in decibels (dB). The SNR 144 may also be a function of the fit of the article 100. Further, the SNR 144 may also be a function of the ambient noise levels.

In one example, the SNR 144 is determined according to the equation provided below:

$$SNR_{dB} = 20\log_{10}\frac{A_{signal}}{A_{noise}} \quad (2)$$

where, $A_{signal}$ is estimated signal power of the noise component; and $A_{noise}$ is estimated signal power of the noise component.

Figure 2C:
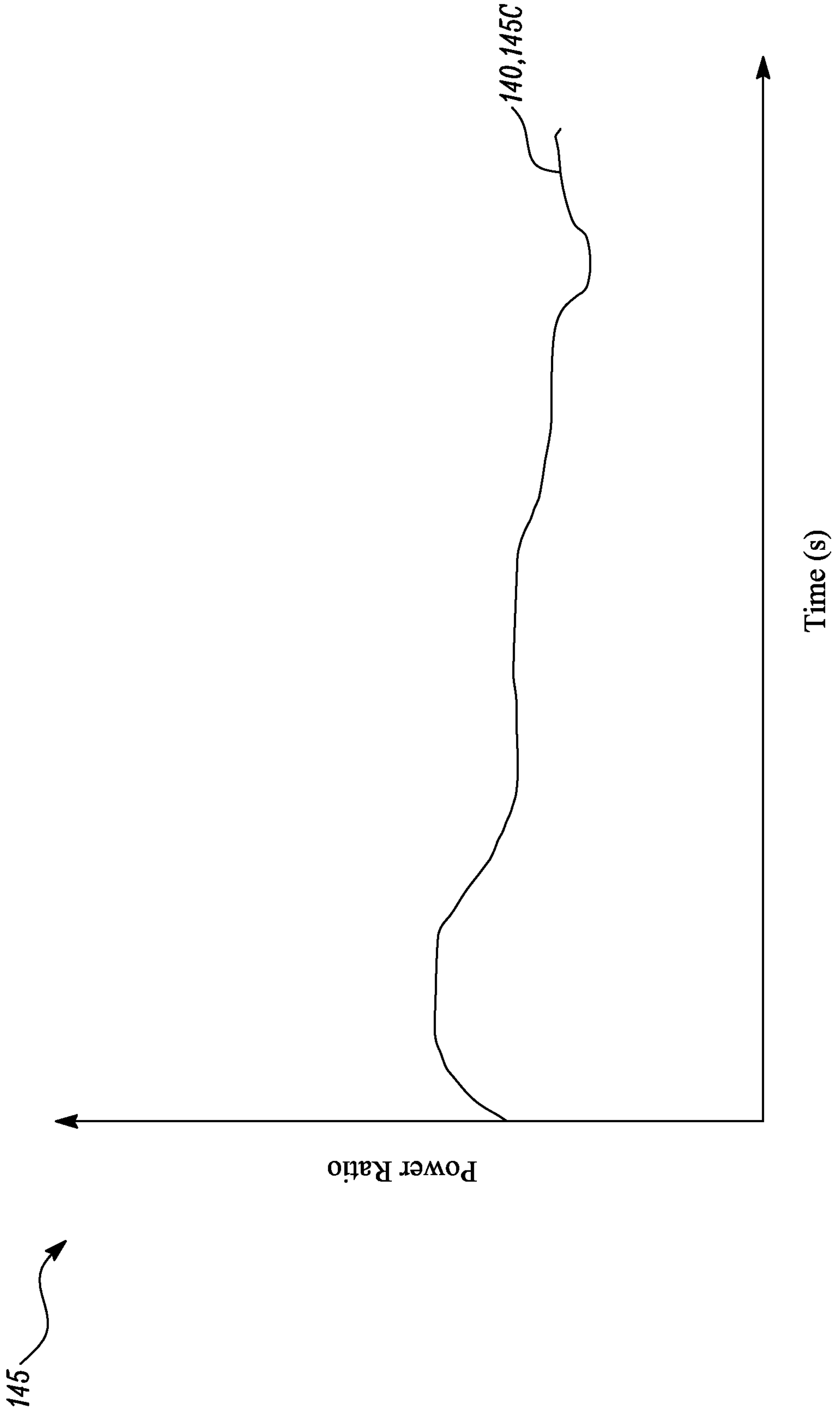
FIG. 2C illustrates a plot depicting a power ratio of an audio power in a predetermined frequency range and an audio power in an out-of-band frequency range of an audio stream, in accordance with an embodiment of the present disclosure.

FIG. 2C illustrates an exemplary plot 145 depicting a power ratio of an audio power in a predetermined frequency range and an audio power in an out-of-band frequency range of an audio stream from the one or more audio streams 112 (shown in FIG. 1). Time is expressed in seconds(s) in the abscissa. Power ratio is shown in the ordinate in arbitrary units. The plot 145 includes a curve 145C representative of the power ratio of the audio power in the predetermined frequency range and the audio power in the out-of-band frequency range of the audio stream with respect to time.

Referring now to FIGS. 1 and 2C, in some examples, the audio stream may be the audio stream 112-1 or the audio stream 112-2. In some embodiments, the one or more evaluation parameters 140 include a corresponding audio power in the out-of-band frequency range outside the predetermined frequency range for each of the one or more audio streams 112. In some embodiments, the processor 130 is configured to determine the score S for the one or more audio streams 112 based on the corresponding audio power in the out-of-band frequency range for each of the one or more audio streams 112.

For example, the processor 130 is configured to determine the score S for the audio stream based on the audio power in the out-of-band frequency range of the audio stream. In some other examples, the processor 130 may be configured to determine the score S for the audio stream based on the power ratio of the audio power in the predetermined frequency range and the audio power in the out-of-band frequency range of the audio stream. In some embodiments, the processor 130 is configured to determine the score S for each of the segments 180 (shown in FIG. 2A) of the audio stream based on the corresponding audio power in the out-of-band frequency range of each of the segments 180 of the audio stream.

As discussed above, the one or more audio streams 112 may include the speech of the user of the article 100. Therefore, ideally the one or more audio streams 112 should lie within the predetermined frequency range of the speech component of the one or more audio streams 112. For example, the predetermined frequency range may be up to about 2 kilohertz (kHz). Therefore, the out-of-band frequency range beyond than the predetermined frequency range may include frequencies from the harmful noise in the environment. The audio power in the out-of-band frequency range may therefore be indicative of the noise component of the one or more audio streams 112. Further, in some examples, the score S may be determined according to the audio power in the out-of-band frequency range. Furthermore, in some other examples, the score S may be determined according to the power ratio.

Figure 3:
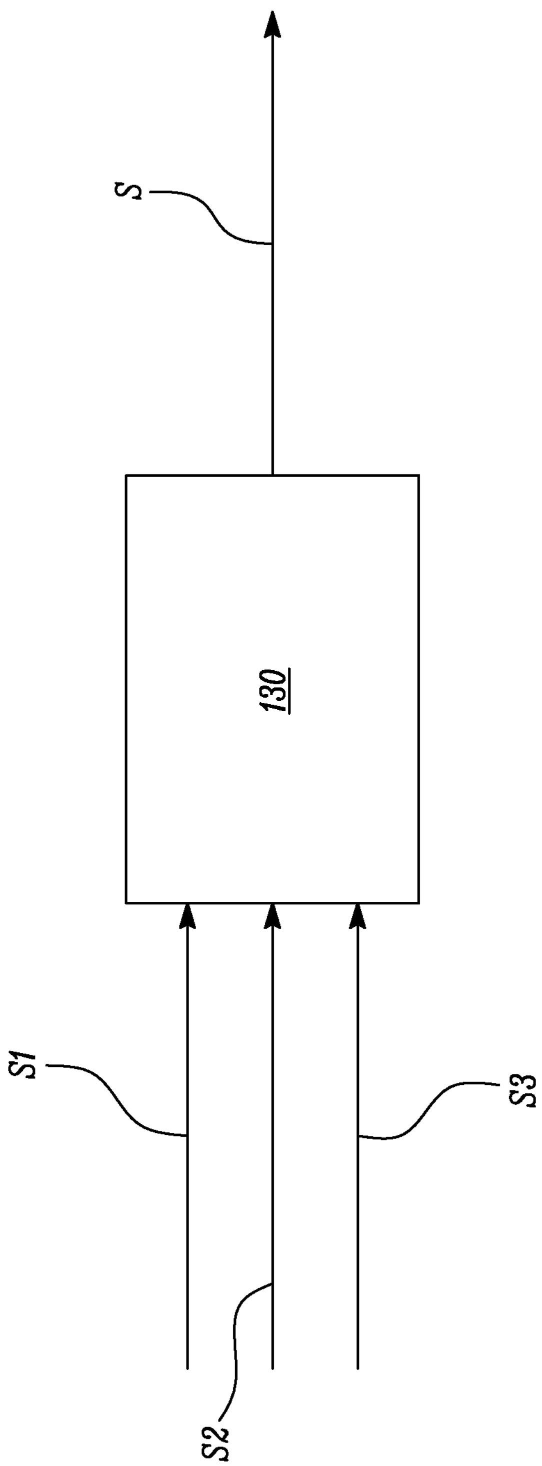
FIG. 3 illustrates a schematic block diagram depicting a processor of the article of PPE, in accordance with an embodiment of the present disclosure.

FIG. 3 illustrates a schematic block diagram depicting the processor 130 of the article 100 shown in FIG. 1, according to an embodiment of the present disclosure.

Referring to FIGS. 1-3, in some embodiments, the processor 130 is configured to determine one or more individual scores corresponding to the one or more evaluation parameters 140. For example, the processor 130 may determine a score S1 corresponding to the baseline noise level 142 of each the one or more audio streams 112, a score S2 corresponding to the SNR 144 of each the one or more audio streams 112, and a score S3 corresponding to the audio power in the out-of-band frequency range of each the one or more audio streams 112.

In some embodiments, the processor 130 is further configured to determine the score S for the one or more audio streams 112 based on the one or more individual scores corresponding to the one or more evaluation parameters 140. For example, the score S for the one or more audio streams 112 may be determined based on one or more of the score S1, the score S2, and the score S3.

In some examples, the score S may be a sum of the one or more individual scores (e.g., one or more of the scores S1-S3). In some other examples, the score S may be a weighted average of the one or more individual scores. However, in some other examples, the score S may be determined using any combination of the one or more individual scores.

Figure 4:
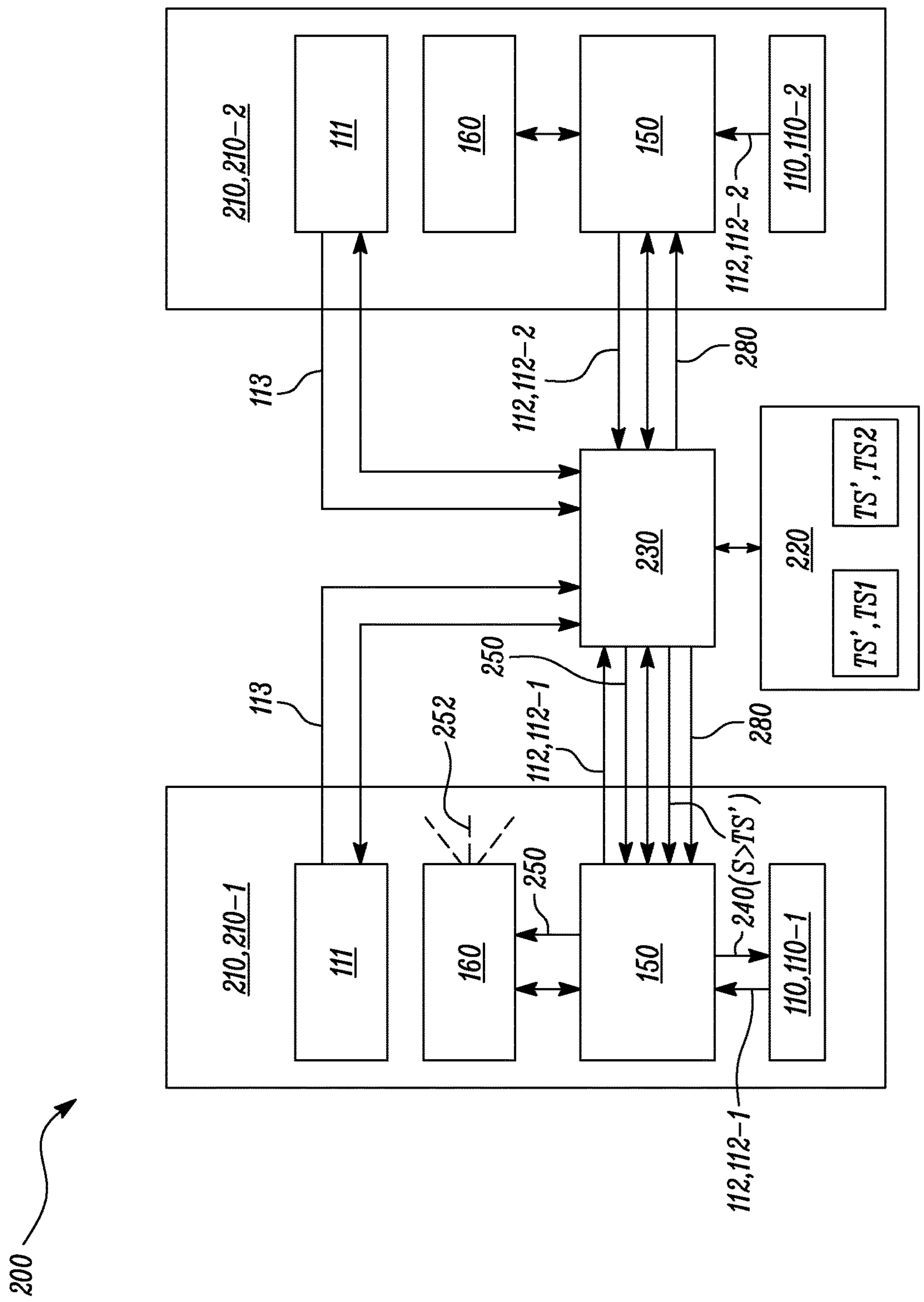
FIG. 4 illustrates a schematic block diagram of a communication system, in accordance with an embodiment of the present disclosure.

FIG. 4 illustrates a schematic block diagram of a communication system 200, according to an embodiment of the present disclosure.

The communication system 200 includes a plurality of articles of PPE 210. The plurality of articles of PPE 210 may interchangeably be referred to as "the plurality of articles 210". In the illustrated embodiment of FIG. 4, the communication system 200 includes two articles 210-1, 210-2. However, in some other embodiments, the communication system 200 may include any number of articles 210. In some embodiments, each of the plurality of articles 210 is the hearing protection device (HPD). In some embodiments, the plurality of articles 210 may be substantially similar to the article 100 (shown in FIG. 1). Common components are referred to by the same reference numerals.

Each of the plurality of articles 210 includes the at least one microphone 110 configured to generate the one or more audio streams 112. In the illustrated embodiment of FIG. 4, the article 210-1 includes the microphone 110-1 and the article 210-2 includes the microphone 110-2. Further, the microphone 110-1 is configured to generate the audio stream 112-1 and the microphone 110-2 is configured to generate the audio stream 112-2. However, the plurality of articles 210 may not include the processor 130 (shown in FIG. 1). Further, each of the plurality of articles 210 includes the transceiver 150 configured to transmit the one or more audio streams 112.

The communication system 200 further includes a memory 220. The memory 220 is configured to store at least one threshold score TS'. The at least one threshold score TS' may be substantially similar to the threshold score TS (shown in FIG. 1). However, in some embodiments, the at least one threshold score TS' may include a plurality of threshold scores corresponding to the plurality of articles 210. In other words, the at least one threshold score TS' includes a corresponding threshold score for each of the plurality of articles 210. For example, in some embodiments, the at least one threshold score TS' includes a threshold score TS1 and a threshold score TS2 corresponding to the two articles 210-1, 210-2. Specifically, the threshold score TS1 corresponds to the article 210-1, while the threshold score TS2 corresponds to the article 210-2.

The communication system 200 further includes a hub 230. The hub 230 is communicably coupled to each of the memory 220 and the transceiver 150 of each of the plurality of articles 210.

For each article 210 from the plurality of articles 210, the hub 230 is configured to receive the one or more audio streams 112. For example, the hub 230 is configured to receive the audio stream 112-1 from the article 210-1 and the audio stream 112-1 from the article 210-2.

For each article 210 from the plurality of articles 210, the hub 230 is configured to determine the score S for the one or more audio streams 112 based the on one or more evaluation parameters 140. For example, the hub 230 is configured to determine respective scores S for the audio streams 112-1, 112-2 based the one or more evaluation parameters 140 (shown in FIGS. 2A-2C and 5).

For each article 210 from the plurality of articles 210, the hub 230 is further configured to compare the score S with the at least one threshold score TS' stored in the memory 220. For example, the hub 230 is configured to compare the respective scores S with the at least one threshold score TS' stored in the memory 220. In some cases, the hub 230 is configured to compare the score S for the audio stream 112-1 received from the article 210-1 with the threshold score TS1.

The hub 230 is further configured to compare the score S for the audio stream 112-2 received from the article 210-2 with the threshold score TS2.

In some embodiments, each of the plurality of articles 210 further includes the external microphone 111 communicably coupled to the hub 230. The external microphone 111 is configured to generate the one or more ambient audio streams 113. For each article 210 from the plurality of articles 210, the hub 230 is further configured to receive the one or more ambient audio streams 113. For each article 210 from the plurality of articles 210, the hub 230 is configured to adjust the corresponding threshold score at least based on the one or more ambient audio streams 113. For example, the hub 230 may adjust the threshold score TS1 at least based on the one or more ambient audio streams 113 received from the article 210-1. The hub 230 may further adjust the threshold score TS2 at least based on the one or more ambient audio streams 113 received from the article 210-2. In some embodiments, the hub 230 may receive the ambient audio streams 113 or one or more measurements based on the ambient audio streams 113 from the respective transceivers 150.

For each article 210 from the plurality of articles 210, the hub 230 is further configured to generate a mute signal 240 when the score S of the one or more audio streams 112 crosses the at least one threshold score TS'. Therefore, the one or more audio streams 112 are not generated by the at least one microphone 110 and thereby not transmitted to the other articles 210. This may prevent the harmful noises from being transmitted to the other articles 210 and protect the ears of the other users of the other articles 210, while also enhancing the communication between the users of the plurality of articles 210.

For example, the hub 230 is configured to generate the mute signal 240 when the score S of any of the audio streams 112-1, 112-2 crosses the at least one threshold score TS'. In a further example, the hub 230 is configured to generate the mute signal 240 when the score S of the audio stream 112-1 crosses the threshold score TS1 and/or the score S of the audio stream 112-2 crosses the threshold score TS2.

For each article 210 from the plurality of articles 210, the hub 230 is further configured to transmit the mute signal 240 to the transceiver 150 of the corresponding article 210 for which the score S crosses the at least one threshold score TS'.

In the illustrated embodiment of FIG. 4, the score S of the audio stream 112-1 received from the article 210-1 crosses the threshold score TS1. Therefore, the hub 230 generates the mute signal 240. Further, as illustrated in FIG. 4, the hub 230 transmits the mute signal 240 to the transceiver 150 of the article 210-1 for which the score S crosses the threshold score TS' or TS1.

Each article 210 from the plurality of articles 210 is configured to mute the corresponding at least one microphone 110 upon receiving the mute signal 240 from the hub 230. For example, the article 210-1 from the plurality of articles 210 is configured to mute the microphone 110-1 upon receiving the mute signal 240 from the hub 230. In some embodiments, the at least one microphone 110-1 may include a plurality of microphones, in such cases, the article 210-1 may mute each of the plurality of microphones upon receiving the mute signal 240 from the hub 230.

In some embodiments, each of the plurality of articles 210 further includes the output device 160 communicably coupled to the transceiver 150. For each article 210 from the plurality of articles 210, the hub 230 is further configured to generate an alert signal 250 when the score S crosses the at least one threshold score TS' and transmit the alert signal 250 to the transceiver 150 of the corresponding article 210. In some embodiments, the alert signal 250 may be substantially similar to the alert signal 170 (shown in FIG. 1). The output device 160 of the corresponding article 210 is configured to generate an alert 252 when the transceiver 150 receives the alert signal 250 from the hub 230. In some embodiments, the alert 252 may be substantially similar to the alert 172 (shown in FIG. 1).

In some embodiments, for each article 210 from the plurality of articles 210, the hub 230 is further configured to segment the one or more audio streams 112 into the one or more segments 180 (shown in FIG. 2A) of the predetermined interval 182 (shown in FIG. 2A). In some embodiments, for each article 210 from the plurality of articles 210, the hub 230 is further configured to determine the score S for the one or more segments 180 of the one or more audio streams 112. In some embodiments, for each article 210 from the plurality of articles 210, the hub 230 is further configured to determine the score S for each of the one or more segments 180 of the one or more audio streams 112.

As discussed above, the one or more evaluation parameters 140 include at least one of the corresponding baseline noise level 142 (shown in FIG. 2A) of each of the one or more audio streams 112, the corresponding SNR 144 (shown in FIG. 2B) of each of the one or more audio streams 112, and the corresponding audio power in the out-of-band frequency range (shown in FIG. 2C) of each of the one or more audio streams 112. However, in some embodiments, the one or more evaluation parameters 140 may further include a corresponding crosstalk level 148 (shown in FIG. 5) of each of the one or more audio streams 112. The corresponding crosstalk level 148 of each of the one or more audio streams 112 is described further in detail with respect to FIG. 5.

In some embodiments, the hub 230 is further configured to mix the one or more audio streams 112 received from each of the plurality of articles 210 to generate a mixed audio stream 280 and transmit the mixed audio stream 280 to the transceiver 150 of each of the plurality of articles 210. Therefore, an audio stream including the harmful noises due to the improper fit may also corrupt the mixed audio stream 280. The communication system 200 including the hub 230, may prevent the audio stream including the harmful noises from being generated and corrupting the mixed audio stream 280. Thus, the users of the other articles 210 may communicate effectively with each other.

In some other embodiments, the hub 230 may not generate the mixed audio stream 280. In other words, the hub 230 may only monitor the one or more audio streams 112 from each of the plurality of articles 210 and transmit the mute signal 240 to the transceiver 150 of the corresponding article 210 for which the score S crosses the at least one threshold score TS'.

Figure 5:
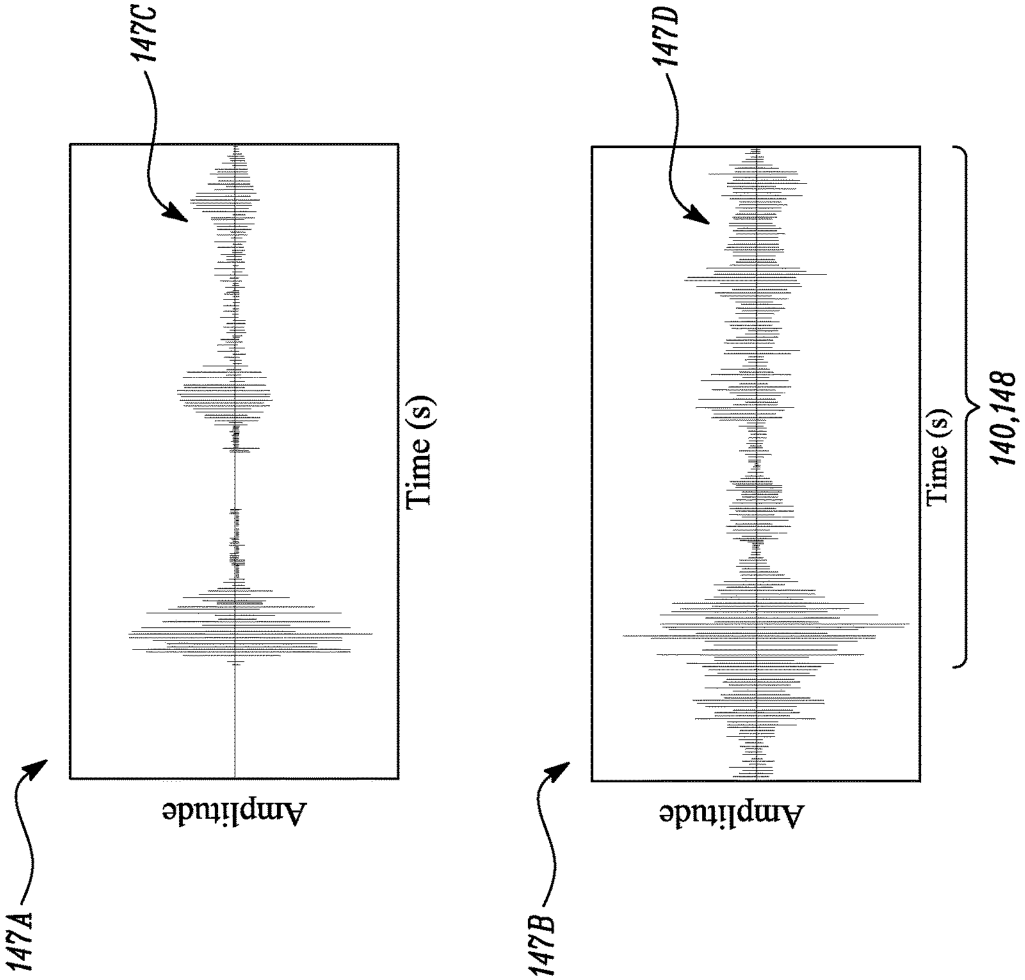
FIG. 5 illustrates plots depicting amplitude versus time of a first audio stream and a second audio stream, respectively, in accordance with an embodiment of the of the present disclosure.

FIG. 5 illustrates exemplary plots 147A, 147B depicting amplitude versus time of audio streams 112-1, 112-2 (shown in FIG. 4) from the plurality of articles 210-1, 210-2 (shown in FIG. 4), respectively. Time is expressed in seconds(s) in the abscissa. Amplitude is shown in the ordinate in arbitrary units. The plot 147A includes a curve 147C representative of the audio stream 112-1 from the article 210-1 with respect to time. The plot 147B includes a curve 147D representative of the audio stream 112-2 from the article 210-1 with respect to time.

Referring now to FIGS. 4 and 5, in some embodiments, the corresponding crosstalk level 148 of each of the one or more audio streams 112 is indicative of a crosstalk of at least a portion of each of the one or more audio streams 112 with at least one portion of the one or more audio streams 112 of any of the other articles 210 from the plurality of articles 210. For each article 210 from the plurality of articles 210, the hub 230 is configured to determine the score S for the one or more audio streams 112 based on the corresponding crosstalk level 148 of each of the one or more audio streams 112.

For example, in the illustrated embodiment of FIG. 5, a portion of the audio stream 112-2 received from the article 210-2 exhibits crosstalk with at least some portion of the audio stream 112-1 received from the article 210-1. The hub 230 may determine the crosstalk level 148 of the audio stream received from the article 210-2. Further, the hub 230 may determine the score S for the audio stream received from the article 210-2 based on the crosstalk level 148. The crosstalk level 148 may be useful when the users of the articles 210 are in close proximity to each other in the environment.

Figure 6:
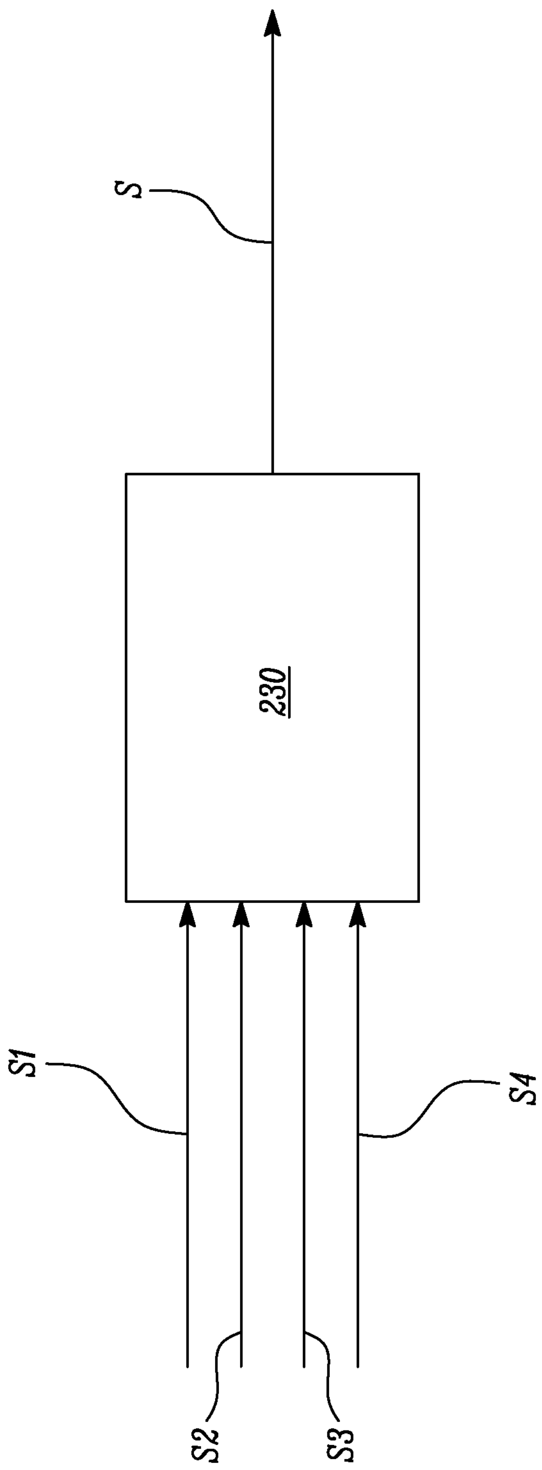
FIG. 6 illustrates a schematic block diagram depicting a hub of the communication system, in accordance with an embodiment of the present disclosure.

FIG. 6 illustrates a schematic block diagram depicting the hub 230 of the communication system 200 shown in FIG. 4, according to an embodiment of the present disclosure.

Referring to FIGS. 2A-2C and 5-6, in some embodiments, for each article 210 from the plurality of articles 210, the hub 230 is configured to determine the one or more individual scores corresponding to the one or more evaluation parameters 140. For example, for each article 210 from the plurality of articles 210, the hub 230 may determine the score S1 corresponding to the baseline noise level 142 of each the one or more audio streams 112, the score S2 corresponding to the SNR 144 of each the one or more audio streams 112, the score S3 corresponding to the audio power in the out-of-band frequency range of each the one or more audio streams 112, and a score S4 corresponding to the crosstalk level 148 of each the one or more audio streams 112.

In some embodiments, for each article 210 from the plurality of articles 210, the hub 230 is further configured to determine the score S for the one or more audio streams 112 based on the one or more individual scores corresponding to the one or more evaluation parameters 140. For example, the score S for the one or more audio streams 112 may be determined based on one or more of the score S1, the score S2, the score S3, and the score S4.

In some examples, the score S may be a sum of the one or more individual scores (e.g., one or more of the scores S1-S4). In some other examples, the score S may be a weighted average of the one or more individual scores. However, in some other examples, the score S may be determined using any combination of the one or more individual scores.

Figure 7:
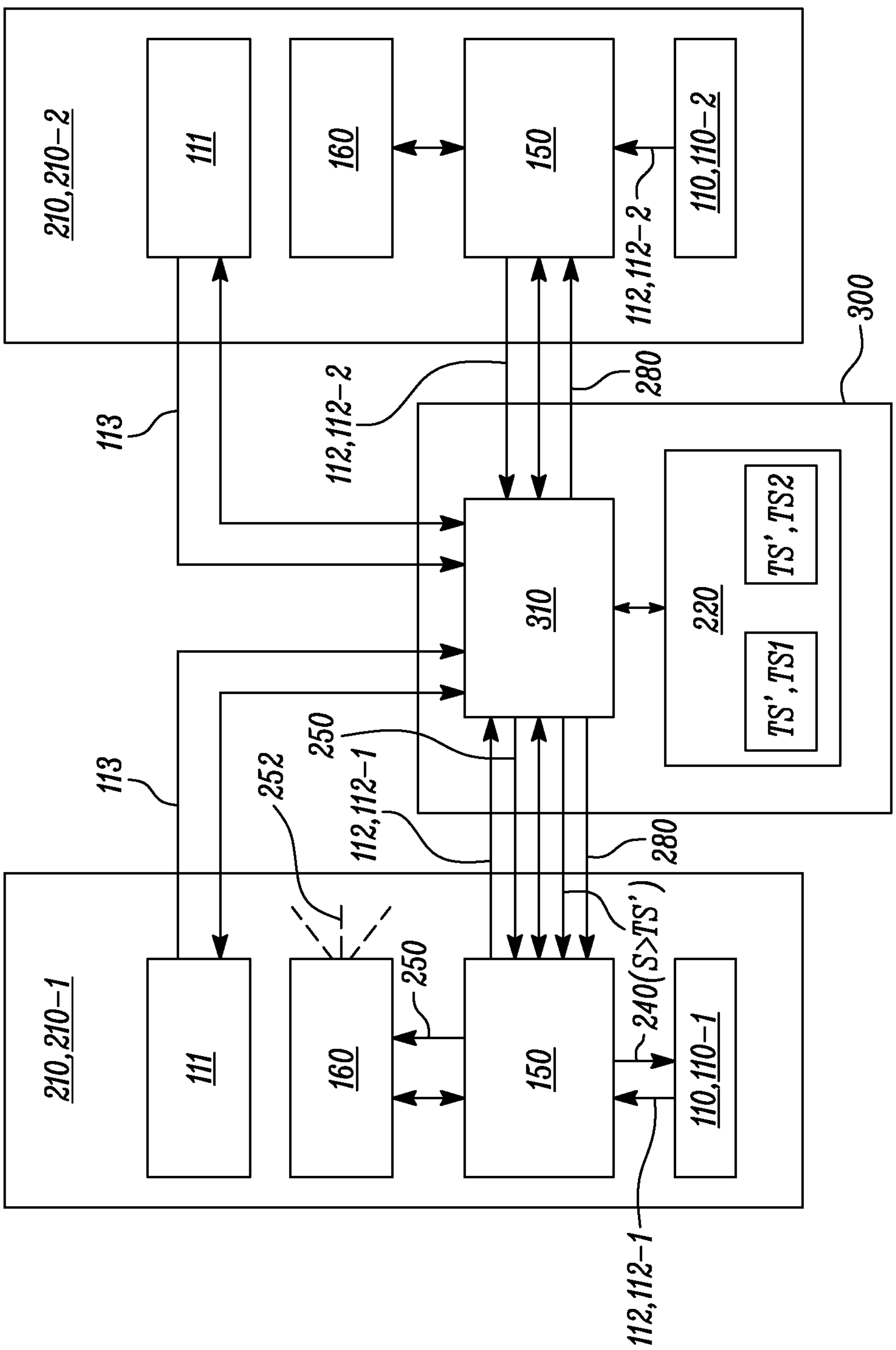
FIG. 7 illustrates a schematic block diagram of a computing device, in accordance with an embodiment of the of the present disclosure.

FIG. 7 illustrates a schematic block diagram of a computing device 300 for controlling the plurality of articles 210, according to an embodiment of the of the present disclosure.

The computing device 300 includes the memory 220 configured to store the at least one threshold score TS'. The computing device 300 further includes a processor 310. The processor 310 is communicably coupled to the memory 220. In some embodiments, the processor 310 may be substantially similar to the hub 230 of the communication system 200 shown in FIG. 4.

The processor 310 is configured to receive the plurality of audio streams 112 transmitted from the plurality of articles 210. Each of the plurality of audio streams 112 is transmitted by a corresponding article 210 from the plurality of articles 210. In some embodiments, the processor 310 is configured to receive the plurality of audio streams 112 transmitted from the transceivers 150 of the plurality of articles 210.

For example, the article 210-1 may transmit the audio stream 112-1 and the article 210-2 may transmit the audio stream 112-2. The processor 310 is configured to receive the audio streams 112-1, 112-2 transmitted from the respective articles 210-1, 210-2.

Further, the processor 310 is configured to determine the plurality of scores S based on the one or more evaluation parameters 140 (shown in FIGS. 2A-2C and 5). The plurality of scores S corresponds to the plurality of audio streams 112. For example, the audio streams 112-1, 112-2 may have respective scores S from the plurality of scores S.

The processor 310 is further configured to compare the plurality of scores S with the at least one threshold score TS' stored in the memory 220. In some embodiments, the processor 310 is further configured to compare each of the plurality of scores S with the threshold score for the corresponding article 210 stored in the memory 220.

The processor 310 is further configured to generate the mute signal 240 when at least one score S from the plurality of scores S corresponding to at least one audio stream 112 from the plurality of audio streams 112 crosses the at least one threshold score TS'. For example, the processor 310 generates the mute signal 240 when the score S from the plurality of scores S corresponding to the audio stream 112-1 from the plurality of audio streams 112 crosses the at least one threshold score TS'.

The processor 310 is further configured to transmit the mute signal 240 to the at least one article 210 transmitting the at least one audio stream 112. For example, when the score S from the plurality of scores S corresponding to the audio stream 112-1 from the plurality of audio streams 112 crosses the at least one threshold score TS', the processor 310 transmits the mute signal 240 to the article 210-1 transmitting the audio stream 112-1.

The at least one article 210 is configured to mute the at least one microphone 110 upon receiving the mute signal 240. For example, upon receiving the mute signal 240, the article 210-1 is configured to mute the microphone 110-1.

Figure 8:
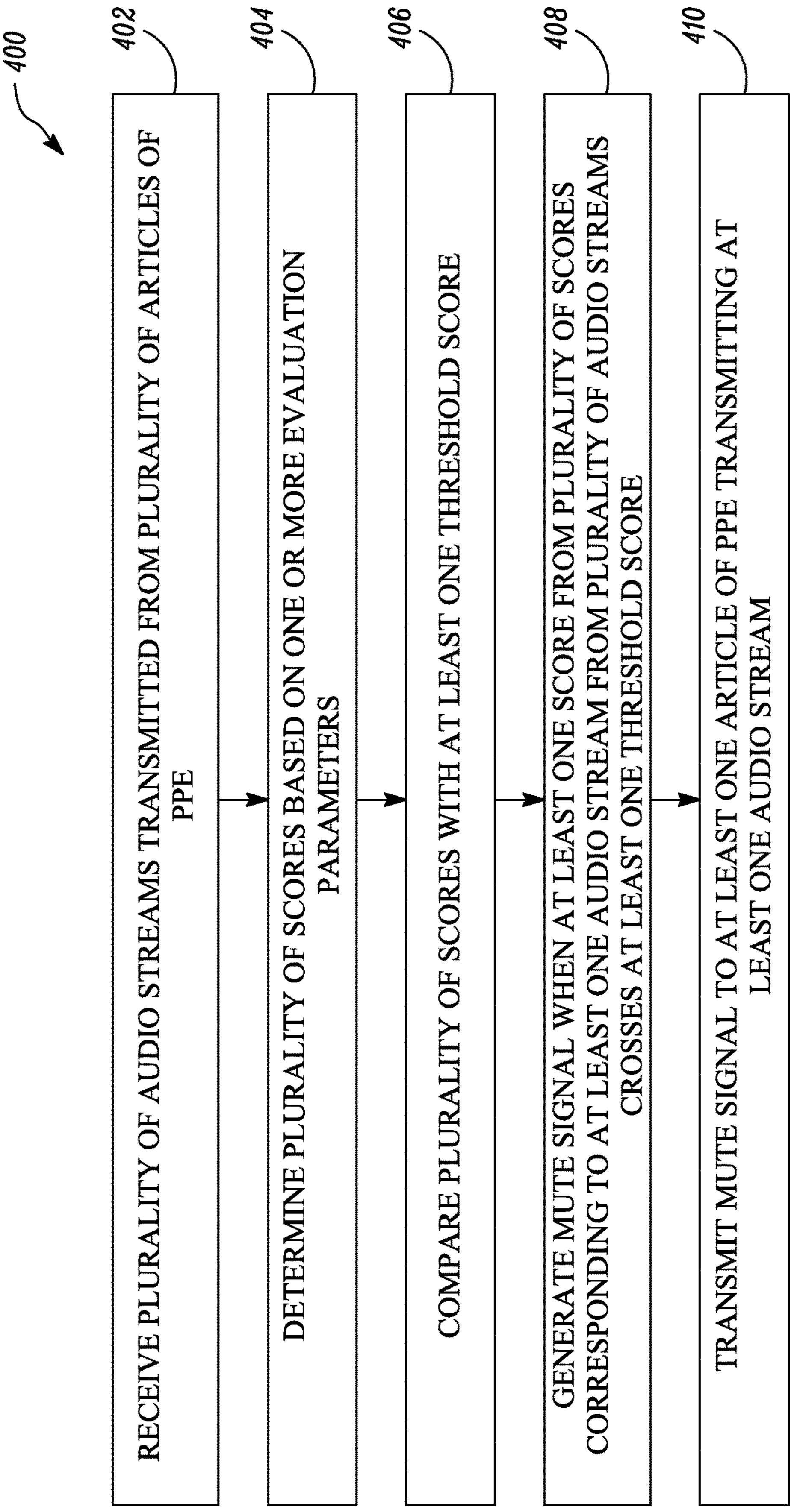
FIG. 8 illustrates a flowchart depicting various steps of a computer-implemented method for controlling a plurality of articles of PPE, in accordance with an embodiment of the present disclosure.

FIG. 8 is a flowchart of a computer-implemented method 400 for controlling the plurality of articles 210. In some embodiments, the computer-implemented method 400 may be implemented in the hub 230 of the communication system 200 shown in FIG. 4 or the processor 310 of the computing device 300 shown in FIG. 7. The computer-implemented method 400 is described with reference to FIGS. 1 to 7.

At step 402, the computer-implemented method 400 includes receiving the plurality of audio streams 112 transmitted from the plurality of articles 210. Each of the plurality of audio streams 112 is transmitted by the corresponding article 210 from the plurality of articles 210.

At step 404, the computer-implemented method 400 includes determining the plurality of scores S based on the one or more evaluation parameters 140. The plurality of scores S corresponds to the plurality of audio streams 112.

At step 406, the computer-implemented method 400 includes comparing the plurality of scores S with the at least one threshold score TS'.

At step 408, the computer-implemented method 400 includes generating the mute signal 240 when at least one score S from the plurality of scores S corresponding to the at least one audio stream 112 from the plurality of audio streams 112 crosses the at least one threshold score TS'.

At step 410, the computer-implemented method 400 includes transmitting the mute signal 240 to the at least one article 210 transmitting the at least one audio stream 112.

Examples

The following illustrative example is merely meant to exemplify the present invention, but it is not intended to limit or otherwise define the scope of the present disclosure.

Five workgroup members donned first, second, third, fourth, and fifth articles (e.g., the articles 210 shown in FIGS. 4 and 7), respectively. Microphones (e.g., the at least one microphone 110 shown in FIGS. 4 and 7) of the first, second, third, fourth, and fifth articles generated first, second, third, fourth, and fifth audio streams (e.g., the one or more audio steams 112 shown in FIGS. 4 and 7). Transceivers (e.g., the transceiver 150 shown in FIGS. 4 and 7) of each of first, second, third, fourth, and fifth articles transmitted the first, second, third, fourth, and fifth audio streams to an external device (e.g., the hub 230 shown in FIG. 4 or the processor 310 shown in 7).

Figure 9:
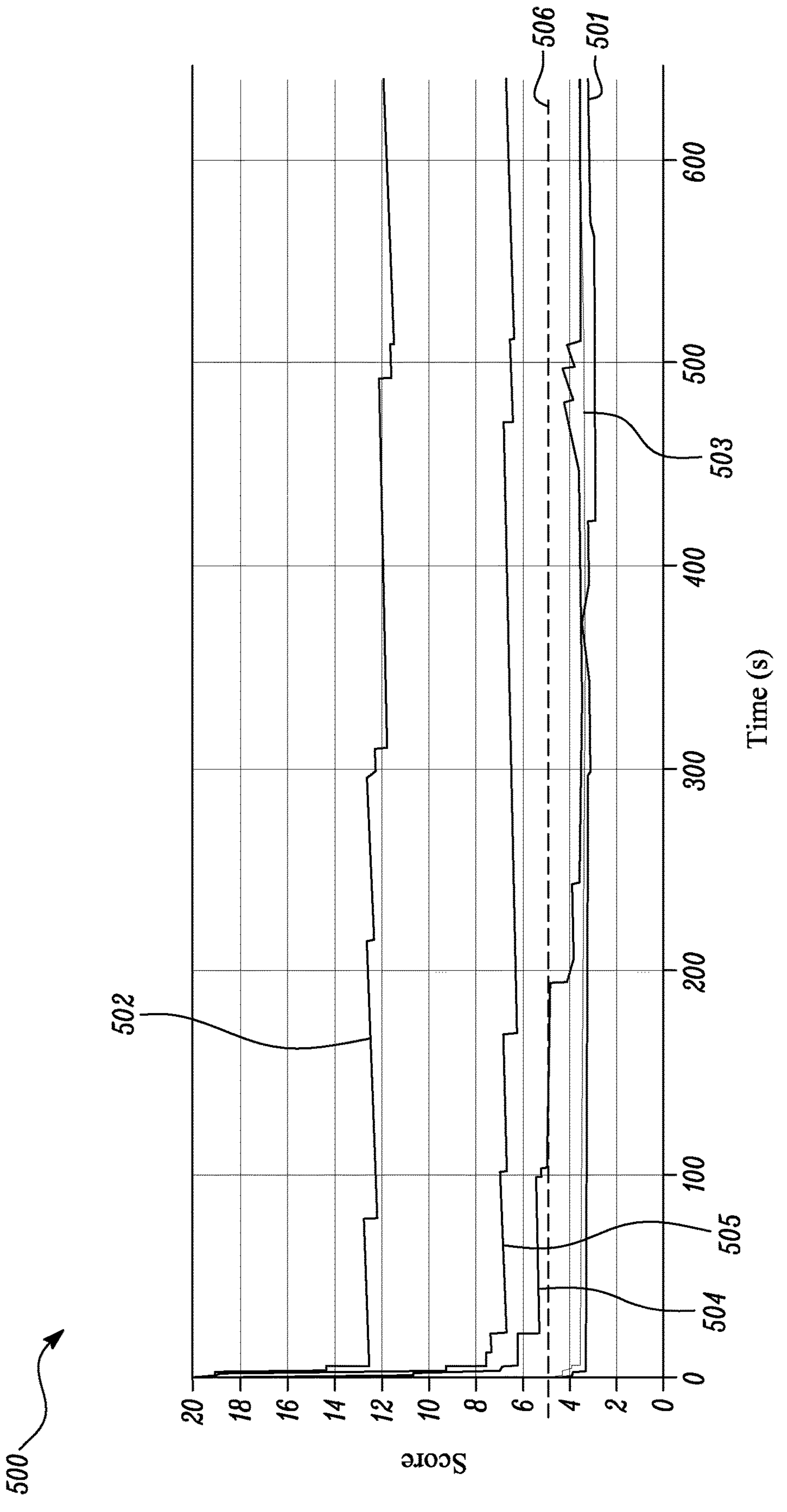
FIG. 9 illustrates a plot depicting scores corresponding to different audio streams with respect to time, in accordance with an embodiment of the present disclosure.

FIG. 9 is a plot 500 depicting scores (e.g., the score S shown in FIGS. 4 and 7) corresponding to the first, second, third, fourth, and fifth of audio streams with respect to time.

Referring now to FIGS. 4 to 9, the plot 500 includes a curve 501 representative of a score of the first article with respect to time. The plot 500 includes a curve 502 representative of a score of the second article with respect to time. The plot 500 includes a curve 503 representative of a score of the third article with respect to time. The plot 500 includes a curve 504 representative of a score of the fourth article with respect to time. The plot 500 includes a curve 505 representative of a score of the fifth article with respect to time. The plot 500 further includes a curve 506 representative of a threshold (e.g., the at least one threshold TS') with respect to time. Time is expressed in seconds(s) in the abscissa. Score is shown in the ordinate. The scores at tenth second are provided in Table 1 below.

TABLE 1

| Article | Known Fit | Score | Predicted Fit | Result |
|---|---|---|---|---|
| First Article | Good | 4.0 | Good | None |
| Second Article | Poor | 18.2 | Poor | Mute |
| Third Article | Good | 4.8 | Good | None |
| Fourth Article | Borderline | 9.1 | Poor | Mute |
| Fifth Article | Poor | 12.5 | Poor | Mute |

A fit of each of the first, second, third, fourth, and fifth articles was examined and noted as shown in the column "Known Fit" in Table 1. The external device predicted the fit of the first, second, third, fourth, and fifth articles based on the corresponding scores.

Specifically, as is apparent from the curves 502, 504, 505, the corresponding scores of the second, fourth, and fifth articles crossed the threshold. Thus, the external device predicted that the fit of each of the second, fourth, and fifth articles was the poor fit. Further, the hub transmitted the mute signal to the second, fourth, and fifth articles having the poor fit. As a result, the microphones of the second, fourth, and fifth articles were muted.

Further, as is apparent from the curves 501 and 503, the corresponding scores of the first and third articles did not cross the threshold. Thus, the external device predicted that the fit of each of the first and third articles was the good fit. Therefore, the hub did not transmit the mute signal to the first and third articles having the good fit. As a result, the microphones of the first and third articles were not muted.

Further as is apparent from the curve 504, the workgroup member donning the fourth article adjusted the fit of the fourth article at about 180th second (three minutes) to the good fit. Thus, the score of the corresponding audio stream reduced below the threshold. Thus, the microphone of the fourth article was not muted after 180th second.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized, and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above or on top of those other elements.

As used herein, when an element, component, or layer for example is described as forming a "coincident interface" with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example. When an element, component, or layer for example is referred to as being "directly on," "directly connected to," "directly coupled with," or "directly in contact with" another element, there are no intervening elements, components or layers for example. The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially.

In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache).

Various examples have been described. These and other examples are within the scope of the following claims.

The invention claimed is:

1. A communication system comprising:

a plurality of articles of PPE, each of the plurality of articles of PPE comprising:

at least one microphone configured to generate one or more audio streams, and a transceiver configured to transmit the one or more audio streams;

a memory configured to store at least one threshold score; and a hub communicably coupled to each of the memory and the transceiver of each of the plurality of articles of PPE, wherein, for each article of PPE from the plurality of articles of PPE, the hub is configured to:

receive the one or more audio streams;

determine a score for the one or more audio streams based on one or more evaluation parameters;

compare the score with the at least one threshold score stored in the memory;

generate a mute signal when the score of the one or more audio streams crosses the at least one threshold score; and transmit the mute signal to the transceiver of the corresponding article of PPE for which the score crosses the at least one threshold score;

wherein each article of PPE from the plurality of articles of PPE is configured to mute the corresponding at least one microphone upon receiving the mute signal from the hub.

2. The communication system of claim 1, wherein the one or more evaluation parameters comprise a corresponding baseline noise level of each of the one or more audio streams, and wherein, for each article of PPE from the plurality of articles of PPE, the hub is configured to determine the score for the one or more audio streams based on the corresponding baseline noise level of each of the one or more audio streams.

3. The communication system of claim 1, wherein the one or more evaluation parameters comprise a corresponding signal-to-noise ratio (SNR) for each of the one or more audio streams, and wherein, for each article of PPE from the plurality of articles of PPE, the hub is configured to determine the score for the one or more audio streams based on the corresponding SNR of each of the one or more audio streams.

4. The communication system of claim 1, wherein the one or more evaluation parameters comprise a corresponding audio power in an out-of-band frequency range outside a predetermined frequency range of each of the one or more audio streams, and wherein, for each article of PPE from the plurality of articles of PPE, the hub is configured to determine the score for the one or more audio streams based on the corresponding audio power in the out-of-band frequency range of each of the one or more audio streams.

5. The communication system of claim 1, wherein the one or more evaluation parameters comprise a corresponding crosstalk level of each of the one or more audio streams, wherein the corresponding crosstalk level of each of the one or more audio streams is indicative of a crosstalk of at least a portion of each of the one or more audio streams with at least one portion of the one or more audio streams of any of the other articles of PPE from the plurality of articles of PPE, and wherein, for each article of PPE from the plurality of articles of PPE, the hub is configured to determine the score for the one or more audio streams based on the corresponding crosstalk level of each of the one or more audio streams.

6. The communication system of claim 1, wherein, for each article of PPE from the plurality of articles of PPE, the hub is further configured to:

determine one or more individual scores corresponding to the one or more evaluation parameters; and determine the score for the one or more audio streams based on the one or more individual scores corresponding to the one or more evaluation parameters.

7. A computing device for controlling a plurality of articles of PPE, the computing device comprising:

a memory configured to store at least one threshold score; and a processor communicably coupled to the memory, the processor configured to:

receive a plurality of audio streams transmitted from the plurality of articles of PPE, each of the plurality of audio streams being transmitted by a corresponding article of PPE from the plurality of articles of PPE;

determine a plurality of scores based on one or more evaluation parameters, wherein the plurality of scores corresponds to the plurality of audio streams;

compare the plurality of scores with at least one threshold score stored in the memory;

generate a mute signal when at least one score from the plurality of scores corresponding to at least one audio stream from the plurality of audio streams crosses the at least one threshold score; and transmit the mute signal to the at least one article of PPE transmitting the at least one audio stream;

wherein the at least one article of PPE is configured to mute at least one microphone upon receiving the mute signal.

* * * * *